(12) United States Patent
Williamson

(10) Patent No.: US 10,386,626 B2
(45) Date of Patent: Aug. 20, 2019

(54) NON-TELECENTRIC MULTISPECTRAL STEREOSCOPIC ENDOSCOPE OBJECTIVE

(71) Applicant: Nikon Corporation, Tokyo (JP)

(72) Inventor: David M. Williamson, Tucson, AZ (US)

(73) Assignee: NIKON CORPORATION, Tokyo (JP)

( * ) Notice: Subject to any disclaimer, the term of this patent is extended or adjusted under 35 U.S.C. 154(b) by 13 days.

(21) Appl. No.: 15/425,455

(22) Filed: Feb. 6, 2017

(65) Prior Publication Data

US 2017/0235120 A1 Aug. 17, 2017

Related U.S. Application Data

(63) Continuation-in-part of application No. 15/393,705, filed on Dec. 29, 2016.

(60) Provisional application No. 62/294,373, filed on Feb. 12, 2016.

(51) Int. Cl.
| | |
|---|---|
| *H04N 13/257* | (2018.01) |
| *G02B 23/24* | (2006.01) |
| *G02B 9/62* | (2006.01) |
| *G02B 13/18* | (2006.01) |
| *A61B 1/04* | (2006.01) |
| *A61B 1/00* | (2006.01) |
| *G02B 13/04* | (2006.01) |
| *H04N 13/239* | (2018.01) |

(52) U.S. Cl.
CPC ........ *G02B 23/243* (2013.01); *A61B 1/00096* (2013.01); *A61B 1/00193* (2013.01); *A61B 1/04* (2013.01); *G02B 9/62* (2013.01); *G02B 13/04* (2013.01); *G02B 13/18* (2013.01); *G02B 23/2415* (2013.01); *H04N 13/239* (2018.05); *H04N 13/257* (2018.05)

(58) Field of Classification Search
None
See application file for complete search history.

(56) References Cited

U.S. PATENT DOCUMENTS

| | | | |
|---|---|---|---|
| 2004/0176662 A1* | 9/2004 | Forkey | A61B 1/00142 600/133 |
| 2004/0233405 A1* | 11/2004 | Kato | G02B 13/143 355/53 |
| 2008/0252997 A1 | 10/2008 | Duckett | |
| 2009/0219631 A1* | 9/2009 | Ning | G02B 9/60 359/716 |
| 2011/0002051 A1 | 1/2011 | Hsu et al. | |
| 2011/0249323 A1 | 10/2011 | Tesar et al. | |

(Continued)

*Primary Examiner* — Eileen M Adams
(74) *Attorney, Agent, or Firm* — Yakov S. Sidorin; Quarles & Brady LLP

(57) ABSTRACT

Non-telecentric in image space optical objective dimensioned to operate as part of intravascular endoscope probe and including first and second groups of lens elements (separated by an aperture stop) each of which has negative optical power. The first group of lens elements includes a first meniscus lens with a positive dioptric power and a first optical doublet. The second group of lens elements includes a sequence of second and third optical doublets and a second meniscus lens that follows the third optical doublet. At least one of the first and second groups of lens elements includes an aspheric refractive surface, thereby reducing distortion down to under 0.25% for field angles up to at least 40 degrees.

19 Claims, 6 Drawing Sheets

(56) References Cited

U.S. PATENT DOCUMENTS

2013/0057666 A1   3/2013   Fujii
2015/0150459 A1*  6/2015   Werahera ............ A61B 5/0075
                                                600/411

* cited by examiner

NON-TELECENTRIC MULTISPECTRAL STEREOSCOPIC ENDOSCOPE OBJECTIVE

CROSS-REFERENCE TO RELATED APPLICATIONS

The present application claims priority from the U.S. Provisional Patent Application No. 62/294,373 filed on Feb. 12, 2016 and titled "Non-Telecentric Multispectal Stereoscopic Endoscope Objective". The present application is also a continuation-in-part from the co-assigned U.S. patent application Ser. No. 15/393,705 filed on Dec. 29, 2016 and titled "Multispectral Stereoscopic Endoscope System and Use of Same". The disclosure of each of the above-mentioned patent documents is incorporated herein by reference.

TECHNICAL FIELD

The present invention relates to lens systems and, in particular, to a fast multispectral endoscope objective configured to achieve high spatial resolution, low level of vignetting and chromatic aberrations across the visible and the near-IR spectral bands.

BACKGROUND

Endoscopes are often used in minimally invasive surgical and/or therapeutic procedures, such as laparoscopy, hysteroscopy, and colonoscopy, for example. Near-infrared (NIR) imaging using endoscopes has been described in the literature for various clinical applications. Often, such an imaging modality utilizes a contrast agent (such as indocyanine green, for example) that absorbs and/or fluoresces in the 700-900 nm range of the NIR. Although the preponderance of optical instruments currently in use are not optimized for both visible (VIS) and NIR light imaging, such instruments may still transmit sufficient NIR light that it may also be desirable to enable the previously described VIS-NIR imaging system for use with these conventional optical instruments. Conventional optical instruments are typically well-corrected for imaging throughout the visible spectrum, but without equivalent correction in the NIR, NIR images acquired with the aforementioned VIS-NIR imaging system through such optical instruments are likely to be of poor quality. Furthermore, although some of the NIR image aberrations introduced by conventional optical instruments may be corrected by applying compensating lens design techniques to the optical couplers, such techniques are typically not powerful enough to correct both the aberrations and the shift in focal plane between the visible and NIR images produced with such instruments.

Related art attempted to address some of the deficiencies by devising endoscope optics in which the imaging quality throughout the visible and NIR portions of the spectrum were balanced. This included examples of objective lenses (US 2008/0252997, US 2011/0002051, US 2013/0057666) and a compensated optical coupler device (US 2011/0249323), to name just a few. While addressing some of existing deficiencies of the endoscope optics, these and other examples resemble each other in that they have substantially low apertures (typically corresponding to F/5 to F/11), which does not provide practically-sufficient diffraction-limited resolution for a wide-spectral-range imaging with sensor pixels dimensioned to about 1.5. microns. In addition, the existing solutions do not effectuate optical correction of monochromatic and chromatic aberrations, as well as barrel distortion, to a level that is below practically-acceptable low level(s).

At the same time, the lens designs provided by the related art (which includes the solution disclosed in the U.S. application Ser. No. 15/393,705) are approximately telecentric at the optical sensor (in the image space) and are configured specifically either for use in endoscopes or laparoscopes that do not include what's known in the art as a "microfly's eye array", or for use with a follow-up telecentric relay lens system (in the case when the optical sensor is proximal to the user/clinician). However, this inevitably translates to the operational requirement that the objective lens be of greater dimension (diameter) than the dimension of the optical sensor (or that the objective lens be bigger than the size of the first image plane). For an endoscope or laparoscope, larger lens diameter is a major disadvantage, as they frustrate the patient and provide no comfort during the procedure. In addition, in a lens system with the telecentric optical design it is more difficult to correct distortion, since there must be negative optical power present in a portion of the lens system preceding the aperture stop and positive optical power in the remaining portion of the lens. Most prior art does not even attempt to correct this distortion. While the U.S. patent application Ser. No. 15/393,705 provides for correction of distortion, it does so with a relatively large, complex design having with multiple aspheric surfaces.

Embodiments of the present invention address these problems.

SUMMARY

Embodiments of the invention provide an endoscope probe that includes a sheath and a first optical objective. Such objective contains an aperture stop and first and second groups of lens elements separated, along the optical axis of the objective, by the aperture stop. The first group of lens elements has negative dioptric power and includes a first meniscus lens with positive dioptric power and a first optical doublet; while the second group of lens elements has negative dioptric power and includes immediately adjacent to one another second and third optical doublets. The objective is non-telecentric in image space.

Embodiments of the invention further provide a method for forming an image. Such method includes the step of transmitting light through a first group of lens elements of a first optical objective disposed within a housing of an endoscope probe to form an intermediate image at a first plane defined by an aperture stop of such first optical objective. The first group having a first meniscus lens element and a first optical doublet, the first group having negative dioptric power. The method further includes a step of transmitting light from the intermediate image through a second group of lens elements of the first optical objective to form a first resulting image at a second plane. The second group includes a sequence of second and third optical doublets, and has negative dioptric power. In one implementation, such first optical objective is non-telecentric in image space.

BRIEF DESCRIPTION OF THE DRAWINGS

The invention will be more fully understood by referring to the following Detailed Description of Specific Embodiments in conjunction with the Drawings, of which.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

It is appreciated that embodiments of the present invention address the problems associated with devising a stereoscopic version of the endoscope (such as, for example, a stereoscopic laparascopic system) that is required to not only simultaneously have high spatial resolution and operate in a broad spectral band, but also have a size smaller than that of an optical imaging sensor of the system. The solution to such problem is provided in a form of a "micro fly's eye lens" on the imaging sensor and a non-telecentric objective lens characterized by a high F/number, low vignetting, low distortion and chromatic aberrations that are substantially corrected across the visible and the near infrared spectral bands.

As known in the art, in some endoscopic imaging systems capable of high resolution simultaneous color and NIR imaging, none of the image sensors (if multiple image sensors are used) or specific pixels of an image sensor (if only a single color image sensor is used) are exclusively dedicated to NIR imaging. One exemplary imaging system utilizes a red, green, blue (RGB) sensor assembly to acquire both color and NIR fluorescence images by employing the red image sensor to, alternately and in rapid succession, acquire both the red light required for the color image and NIR light required for the NIR image. This imaging system is intended to be used in conjunction with image-projecting optical instruments such as endoscopes, microscopes, colposcopes, etc. that have also been optimized for both visible light and NIR imaging applications. Specifically, the optical instruments (i.e. endoscopes, microscopes, colposcopes, etc.) and the optical assemblies (optical couplers) that couple these instruments to the sensor assembly of the imaging system are constructed using appropriate visible and NIR transmitting optical materials and antireflection coatings and are optically designed to transmit visible and NIR images for which chromatic and geometric aberrations are minimized.

Figure 1:
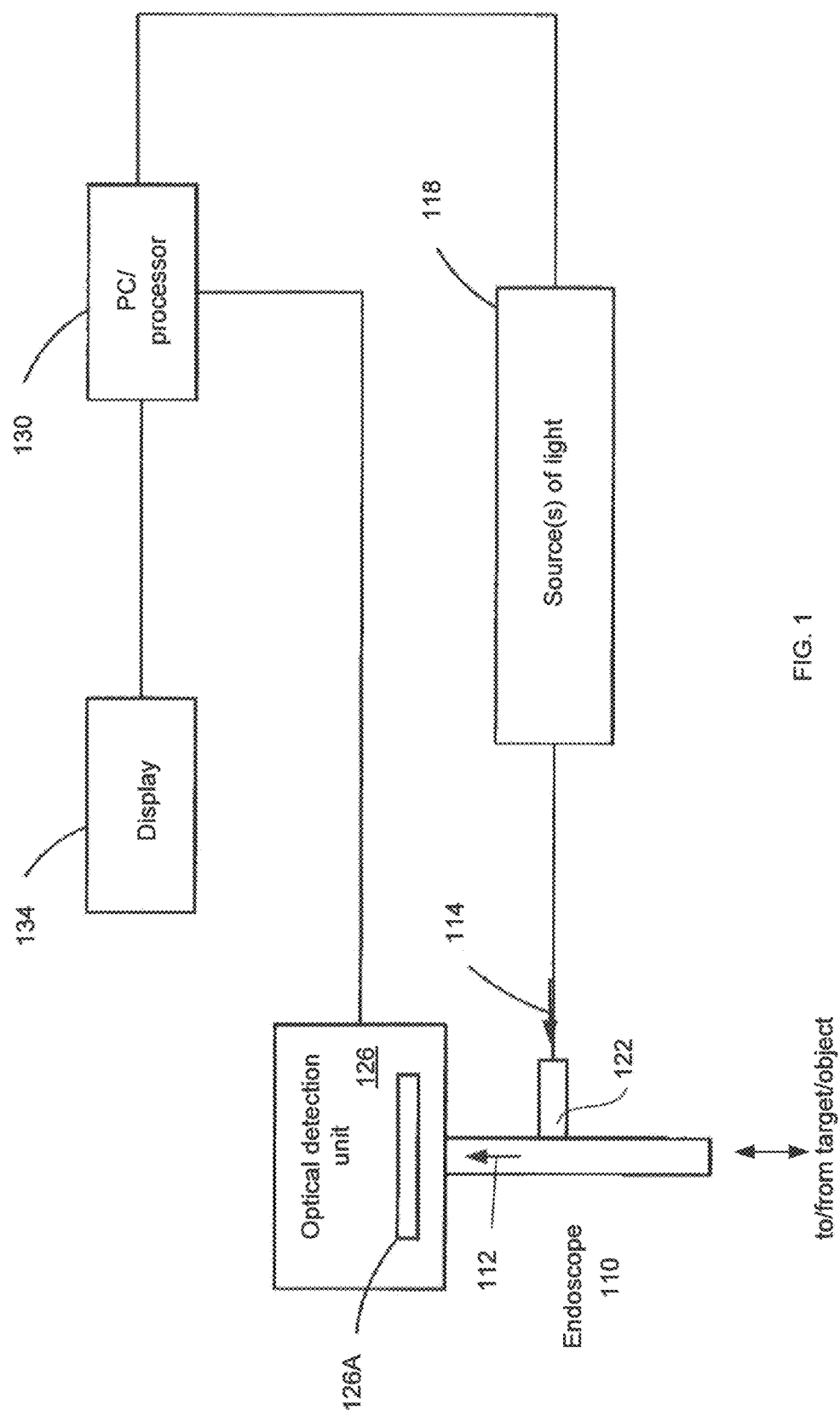
FIG. 1 is a schematic diagram of an endoscope-based optical imaging system.

FIG. 1 depicts a typical schematic configuration of an overall optical instrument 100 (an endoscope-employing optical imaging system), with which an embodiment of the invention can be utilized. The device 100, representing an optical imaging system that employs an endoscope/optical probe 110, is configured to collect and deliver light 112 (received from the target in response to irradiation of the target with light 114 from the source(s) of light 118 via the optical coupler 122) to the optical detection unit 126 with the optical sensor 126A. Additional sub-systems may be present, depending on particular implementation of the instrument 100.

In practice, the endoscope 110 is placed in the proximity of a target or object (such as the subject's tissue, for example inside a natural or created opening in the subject). The system may have one or more illumination sources 118 (such as high-power laser diodes, for example). The light source 118 is configured to emit radiation having wavelengths in the visible and/or infrared portions of the spectrum. Infrared radiation delivered towards the target at predetermined wavelengths may excite a fluorescent dye that has been associated with (affixed or adhered to) the target and cause the fluorescent light to be emitted and collected by the objective of the endoscope 110. In one embodiment, imaging may be performed in multiple discrete spectral bands, for example in two distinct infrared bands, in the infrared spectral band and two visible bands, or in the two infrared and a visible spectral bands, to name just a few examples.

The operation of at least the source(s) of light 118 and the optical detection unit 126 is typically governed by judiciously-designed electronic circuitry that may include a programmable processor 130 in operable communication with tangible, non-transitory computer-readable storage medium carrying program code thereon. The processor 130 may be further configured to perform processing of data received from the optical detection unit 126, as directed by the program code on the storage medium, and to communicate these data and/or the results of the data processing to display system 134 (such as a monitor, for example) to display the data/results thereon.

In one implementation, light at both visible and infrared wavelengths is delivered from the sources 110 to the target (not shown). The one or more illumination sources 118 are configured in operable communication with the PC or programmable processor 130 configured to govern the operation of the sources 118, to collect optical data from the detection unit 126, and to process the collected data to acquire information about the target.

In one implementation, the illumination sources 118 are coupled to the existing fiber optics in the endoscope or wand or coupled to an external cannula embedded with fiber optics or containing a working channel with sufficient diameter to place a fiber optic or fiber optic probe for the transmission of light at an excitation wavelength towards the target/object. The endoscope itself may contain a working channel sufficiently large for a laser fiber to be inserted and in that case a supplementary cannula or sheath for an excitation source would not be required.

TABLE 1A

| ELEMENT NUMBER | RADIUS OF CURVATURE | | THICKNESS | APERTURE DIAMETER | | $n_d$ | $V_d$ |
|---|---|---|---|---|---|---|---|
| | FRONT | BACK | | FRONT | BACK | | |
| OBJECT | | INF | 50.0000 | | | | |
| 1 | 8.1997 CX | A(1) | 0.2000 | 3.0046 | 2.4197 | 1.88660 | 35.0 |
| | | | 0.8234 | | | | |
| 2 | −32.9231 CC | 3.4946 CC | 0.2000 | 2.3944 | 2.3785 | 1.59240 | 68.3 |
| | | | 0.1549 | | | | |
| 3 | 2.1633 CX | 5.4413 CC | 1.2998 | 2.5156 | 2.0938 | 1.81000 | 41.0 |
| 4 | 5.4413 CX | A(2) | 1.0259 | 2.0938 | 1.6743 | 2.00170 | 20.6 |
| | | | 0.4489 | | | | |
| | APERTURE STOP | | | 1.5420 | | | |
| | | | 0.0708 | | | | |
| 5 | 2.3700 CX | 1.5320 CC | 0.2000 | 1.8607 | 1.8951 | 1.85060 | 41.6 |
| 6 | 1.5320 CX | −2.3902 CX | 1.6604 | 1.8951 | 2.3232 | 1.59240 | 68.3 |
| | | | 0.1000 | | | | |
| 7 | 4.2639 CX | −1.5713 CX | 1.6624 | 2.3368 | 2.1642 | 1.45880 | 90.0 |
| 8 | −1.5713 CC | 38.2137 CC | 0.2000 | 2.1642 | 2.2610 | 1.71430 | 38.9 |
| | | | 1.4227 | | | | |
| 9 | A(3) | −3.3581 CX | 0.3830 | 2.5536 | 2.9941 | 1.77200 | 50.0 |
| | | | 0.5000 | | | | |
| 10 | INF | INF | 0.1000 | 3.7587 | 3.8171 | 1.45850 | 67.8 |
| | IMAGE DISTANCE = | | 0.2514 | | | | |
| IMAGE | | INF | | 4.0450 | | | |

NOTES
Positive radius indicates the center of curvature is to the right
Negative radius indicates the center of curvature is to the left
Dimensions are given in millimeters
Thickness is axial distance to next surface
Image diameter shown above is a paraxial value, it is not a ray traced value
$n_d$ denotes a refractive index of the chosen material at a wavelength of a d-line of optical spectrum, while $V_d$ denotes dispersion or the Abbe number at the same wavelength.

Aspheric constants $$Z = \frac{(CURV)Y^2}{1 + (1 - (1+K)(CURV)^2 Y^2)^{1/2}} + (A)Y^4 + (B)Y^6 + (C)Y^8 + (D)Y^{10}$$

| ASPHERIC | CURV | K | A | B | C | D |
|---|---|---|---|---|---|---|
| A(1) | 0.65900863 | 0.00000000 | −5.11571E−03 | −1.69659E−02 | 1.06248E−02 | −4.87109E−03 |
| A(2) | 0.16239829 | 0.00000000 | 2.88740E−02 | 9.77809E−03 | −1.42912E−04 | 6.72231E−03 |
| A(3) | −0.36561884 | 0.00000000 | −3.46977E−02 | −4.08369E−03 | −9.26952E−04 | −4.32918E−04 |

REFERENCE WAVELENGTH = 546.0 NM
SPECTRAL REGION = 435.0-656.0 NM
INFINITE CONJUGATES
EFL = 2.3600
BFL = 0.1430
FFL = 0.1858
F/NO = 2.9412
AT USED CONJUGATES
REDUCTION = 0.0470
FINITE F/NO = 3.0146
OBJECT DIST = 50.0000
TOTAL TRACK = 60.7036
IMAGE DIST = 0.2514
OAL = 10.4522
PARAXIAL
IMAGE HT = 2.0247
IMAGE DIST = 0.2540
SEMI-FIELD
ANGLE = 40.0000
ENTR PUPIL
DIAMETER = 0.8024
DISTANCE = 1.4369
EXIT PUPIL
DIAMETER = 1.5135
DISTANCE = −4.3085

NOTES
FFL is measured from the first surface
BFL is measured from the last surface

TABLE 1B

POLYCHROMATIC WAVEFRONT ANALYSIS OVER VISIBLE SPECTRUM

|  |  |  |  |  |
|---|---|---|---|---|
| X REL. FIELD | 0.00 | 0.00 | 0.00 | 0.00 |
| Y REL. FIELD | 0.00 | 0.56 | 0.69 | 1.00 |
| WEIGHTS | 1.00 | 1.00 | 1.00 | 1.00 |
| NUMBER OF RAYS | 948 | 712 | 632 | 452 |
| WAVELENGTHS | 656.0 | 546.0 | 435.0 |  |
| WEIGHTS | 1 | 2 | 1 |  |

|  |  |  | BEST INDIVIDUAL FOCUS |  |  | BEST COMPOSITE FOCUS |  |  |  |
|---|---|---|---|---|---|---|---|---|---|
|  | FIELD |  | SHIFT | FOCUS | RMS |  | SHIFT | FOCUS | RMS |  |
|  | FRACT | DEG | (MM.) | (MM.) | (WAVES) | STREHL | (MM.) | (MM.) | (WAVES) | STREHL |
| X | 0.00 | 0.00 | 0.000000 | −0.001406 | 0.0177 | 0.988 | 0.000000 | −0.000143 | 0.0204 | 0.984 |
| Y | 0.00 | 0.00 | 0.000000 |  |  |  | 0.000000 |  |  |  |
| X | 0.00 | 0.00 | 0.000000 | 0.001153 | 0.0281 | 0.969 | 0.000000 | −0.000143 | 0.0294 | 0.966 |
| Y | 0.56 | 25.01 | 0.000306 |  |  |  | −0.000068 |  |  |  |
| X | 0.00 | 0.00 | 0.000000 | 0.001501 | 0.0285 | 0.969 | 0.000000 | −0.000143 | 0.0303 | 0.964 |
| Y | 0.69 | 30.01 | 0.000485 |  |  |  | −0.000133 |  |  |  |
| X | 0.00 | 0.00 | 0.000000 | −0.000386 | 0.0401 | 0.939 | 0.000000 | −0.000143 | 0.0401 | 0.938 |
| Y | 1.00 | 40.02 | −0.000017 |  |  |  | 0.000128 |  |  |  |

COMPOSITE RMS FOR POSITION 1: 0.02906

TABLE 1C

MONOCHROMATIC WAVEFRONT ANALYSIS AT 546.0 nm WAVELENGTH

|  |  |  |  |  |
|---|---|---|---|---|
| X REL. FIELD | 0.00 | 0.00 | 0.00 | 0.00 |
| Y REL. FIELD | 0.00 | 0.56 | 0.69 | 1.00 |
| WEIGHTS | 1.00 | 1.00 | 1.00 | 1.00 |
| NUMBER OF RAYS | 316 | 238 | 212 | 154 |
| WAVELENGTHS | 656.0 | 546.0 | 435.0 |  |
| WEIGHTS | 0 | 1 | 0 |  |

|  |  |  | BEST INDIVIDUAL FOCUS |  |  | BEST COMPOSITE FOCUS |  |  |  |
|---|---|---|---|---|---|---|---|---|---|
|  | FIELD |  | SHIFT | FOCUS | RMS |  | SHIFT | FOCUS | RMS |  |
|  | FRACT | DEG | (MM.) | (MM.) | (WAVES) | STREHL | (MM.) | (MM.) | (WAVES) | STREHL |
| X | 0.00 | 0.00 | 0.000000 | −0.001361 | 0.0090 | 0.997 | 0.000000 | −0.001293 | 0.0090 | 0.997 |
| Y | 0.00 | 0.00 | 0.000000 |  |  |  | 0.000000 |  |  |  |
| X | 0.00 | 0.00 | 0.000000 | −0.000654 | 0.0169 | 0.989 | 0.000000 | −0.001293 | 0.0174 | 0.988 |
| Y | 0.56 | 25.00 | −0.000353 |  |  |  | −0.000537 |  |  |  |
| X | 0.00 | 0.00 | 0.000000 | −0.000768 | 0.0101 | 0.996 | 0.000000 | −0.001293 | 0.0106 | 0.996 |
| Y | 0.69 | 30.00 | −0.000548 |  |  |  | −0.000745 |  |  |  |
| X | 0.00 | 0.00 | 0.000000 | −0.003395 | 0.0178 | 0.988 | 0.000000 | −0.001293 | 0.0207 | 0.983 |
| Y | 1.00 | 40.00 | −0.002118 |  |  |  | −0.000871 |  |  |  |

COMPOSITE RMS FOR POSITION 1: 0.01427
Units of RMS are waves at 546.1 nm.
NOTE
Strehl is the intensity at the peak of the point image as a fraction of the peak of the aberration-free image with the same vignetting and obscuration. The approximation used here is generally valid for RMS < 0.1.

TABLE 1D

MONOCHROMATIC WAVEFRONT ANALYSIS AT 1200 nm WAVELENGTH

|  |  |  |  |  |
|---|---|---|---|---|
| X REL. FIELD | 0.00 | 0.00 | 0.00 | 0.00 |
| Y REL. FIELD | 0.00 | 0.56 | 0.69 | 1.00 |
| WEIGHTS | 1.00 | 1.00 | 1.00 | 1.00 |
| NUMBER OF RAYS | 316 | 238 | 212 | 136 |
| WAVELENGTHS | 1200.0 |  |  |  |
| WEIGHTS | 1 |  |  |  |

TABLE 1D-continued

MONOCHROMATIC WAVEFRONT ANALYSIS AT 1200 nm WAVELENGTH

| | | BEST INDIVIDUAL FOCUS | | | | BEST COMPOSITE FOCUS | | | |
|---|---|---|---|---|---|---|---|---|---|
| FIELD | | SHIFT | FOCUS | RMS | | SHIFT | FOCUS | RMS | |
| FRACT | DEG | (MM.) | (MM.) | (WAVES) | STREHL | (MM.) | (MM.) | (WAVES) | STREHL |
| X 0.00 | 0.00 | 0.000000 | −0.004669 | 0.0057 | 0.999 | 0.000000 | −0.003566 | 0.0067 | 0.938 |
| Y 0.00 | 0.00 | 0.000000 | | | | 0.000000 | | | |
| X 0.00 | 0.00 | 0.000000 | −0.003010 | 0.0124 | 0.994 | 0.000000 | −0.003566 | 0.0125 | 0.994 |
| Y 0.56 | 25.00 | −0.001276 | | | | −0.001434 | | | |
| X 0.00 | 0.00 | 0.000000 | −0.001919 | 0.0193 | 0.985 | 0.000000 | −0.003566 | 0.0197 | 0.985 |
| Y 0.69 | 30.00 | −0.001361 | | | | −0.001971 | | | |
| X 0.00 | 0.00 | 0.000000 | −0.002835 | 0.0291 | 0.967 | 0.000000 | −0.003566 | 0.0291 | 0.967 |
| Y 1.00 | 40.00 | −0.002413 | | | | −0.002850 | | | |

COMPOSITE RMS FOR POSITION 1: 0.01665
Units of RMS are waves at 1200.0 nm.
NOTE
Strehl is the intensity at the peak of the point image as a fraction of the peak of the aberration-free image with the same vignetting and obscuration. The approximation used here is generally valid for RMS < 0.1.

Several notes are in order concerning an objective utilized in an embodiment of the endoscope of the invention. Tables 1A, 1B, 1C, and 1D provide data representing an optical train (sequence) of lens elements of an embodiment 200 of FIG. 2, forming a multispectral endoscope objective. The design prescriptions for the embodiments were generated with Code V and are discussed in reference to corresponding figures. In these Tables, optical elements and, possibly, media separating some of the elements, are numbered in a "backward" fashion, starting from that which is the closest to the object/target plane (to which light is delivered in operation from the source of light 118, FIG. 1) towards the plane of the optical sensor 126A. Such approach to numbering of the optical elements makes it easier, as would be appreciated by a skilled artisan, to define the NA and a parameters characterizing non-telecentricity in the image space—that is, in the space of the optical sensor—during the process of optical design. The closest to the object lens element is labeled as element 1 both in Table 1A and FIG. 2; the next lens elements is element 2, and so on, while the plane of the optical sensor is referred to as an image plane and labeled as "I". Positive radius value for a given surface indicates that the center of curvature of such surface is to the right of the surface, while a negative radius value indicates that the center of curvature is to the left of the surface; dimensions are provided in millimeters; thickness is defined as an axial distance from a given surface to the next surface; and an indicated image diameter is a paraxial value and not a ray-traced value. Furthermore, with respect to decentering constants, a decenter defines a new coordinate system (displaced and/or rotated) in which subsequent surfaces are defined. Surfaces following a decenter are aligned on the local mechanical axis (z-axis, for example) of the new coordinate system. The new mechanical axis remains in use for referencing purposes until expressly changed by another decenter. The order in which displacements and tilts are applied to a given surface is specified using different decenter types and these generate different new coordinate systems; those used in this disclosure are explained below. Alpha, beta, and gamma values are presented in degrees. Aspheric surfaces as labeled as $A_j$, and the aperture stop is denoted as S. Notations (both in drawings and description) referring to "R", "G", and "B" refer to wavelengths of about 643.85 nm, 546.1 nm, and 479.99 nm. Additionally, with respect to chromatic aberrations, a reduction in Strehl ratio between monochromatic and polychromatic designs represents the contrast loss from chromatic aberrations over the specified spectral band, while a variation in best individual focus shows the residual field curvature. In Tables, $n_d$ denotes a refractive index and $V_d$ denotes Abbe number at d-line of optical spectrum.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. When used in reference to a numerical value, represent a range of plus or minus 20% with respect to the specified value, more preferably plus or minus 10%, even more preferably plus or minus 5%, most preferably plus or minus 2% with respect to the specified value.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes. In some specific cases, which are within the scope of the invention, the terms "approximately" and "about", when used in reference to a numerical value, represent a range of plus or minus 20% with respect to the specified value, more preferably plus or minus 10%, even more preferably plus or minus 5%, most preferably plus or minus 2% with respect to the specified value.

An non-telecentric endoscope objective 200 structured as described in the above Tables 1A through 1D has an effective focal length of 2.37 mm, which results (for a full diagonal field of view of 80 degrees and in the absence of significant distortion) in formation of an image across a 4 mm diagonal rectangular active area on an optical sensor 126A. Notably, the design provides for an optical image sensor that is larger than the largest clear aperture among the clear apertures of lens elements of the system 200. The F/number achieved in this design is about 2.2, which (in operation at a wavelength of 550 nm) enables a diffraction-limited Airy disc with a diameter of the first dark ring of 1.5 microns; and twice that, 3.0 microns, during the operation of the objective at a 1200 nm wavelength. It can be used with a 1080p high-definition visible and near-IR sensor with 1.8 pixel pitch. In order to implement a stereoscopic system in an endoscope device, two of these objectives are used in parallel, with two sensors (126A and another, not shown in FIG. 1), each receiving optical from a corresponding objective at the optical detection unit. For example, in the embodiment where two optical sensors are used, the optical detection unit includes a first optical sensor configured to receive and detect visible light and a second optical sensor configured to receive and detect light in a different spectral region—for example, infrared light.

The optical objective 200 includes first and second groups of lens elements and an optical plate (element 10), where the first group 210-1 of lens elements preceding the aperture stop S (as viewed from the object) includes a first meniscus 212 (element 1) with a negative dioptric power, a second meniscus 214 (element 2) with a positive dioptric power, and a first optical doublet 216. Notably, and contradistinction with designs of related art, the first group of lens elements 210-1 preceding the aperture stop aggregately possesses a negative dioptric power. The second group 210-2 of lens elements, which includes a sequence of second and third optical doublets 218 and 220, followed by a second meniscus 222 (element 9) having negative dioptric power. The group 210-2 of lens element has, aggregately, a positive optical power—elements 218 and 220 both have positive optical power, overriding the negative power of the element 222.

The second group 210-2 of lens elements is followed by a plane parallel optical plate (element 10) used and configured to protect and seal the surface of the optical sensor. The element 10 can be configured as a protective optical window for the sensor behind it, and/or can be structured as a spectral (color) filter.

The aperture stop S is defined between the first and second optical doublets 216, 218. Notably, the second group 210-2 of lens elements also has a negative dioptric power, which further facilitates correction of the figure of distortion of the overall lens system 200.

Generally, at least one of the groups of lens elements of the endoscope objective (the one preceding the aperture stop S and the one located behind the aperture stop S, as viewed from the object) configured according to the idea of the invention includes an aspheric refractive surface.

Accordingly, a process of formation of an image with the use of the endoscope containing the embodiment 200 of the objective includes the steps of (i) transmitting light through a first group of lens elements of a first optical objective disposed within a housing of an endoscope to a first plane (pupil; plane) defined by an aperture stop of the first optical objective (where the first group has a first meniscus lens element and a first optical doublet) and (ii) transmitting light from the aperture stop through a second group of lens elements of the first optical objective to form an image at a second plane (where the second group including a sequence of second and third optical doublets). In doing so, transmitting light through the first group of lens elements includes transmitting light through the first meniscus lens having a negative dioptric power while transmitting light through the second group of lens elements includes transmitting light through a second meniscus lens positioned between the sequence of identified second and third optical doublets and the second plane.

Figure 2:
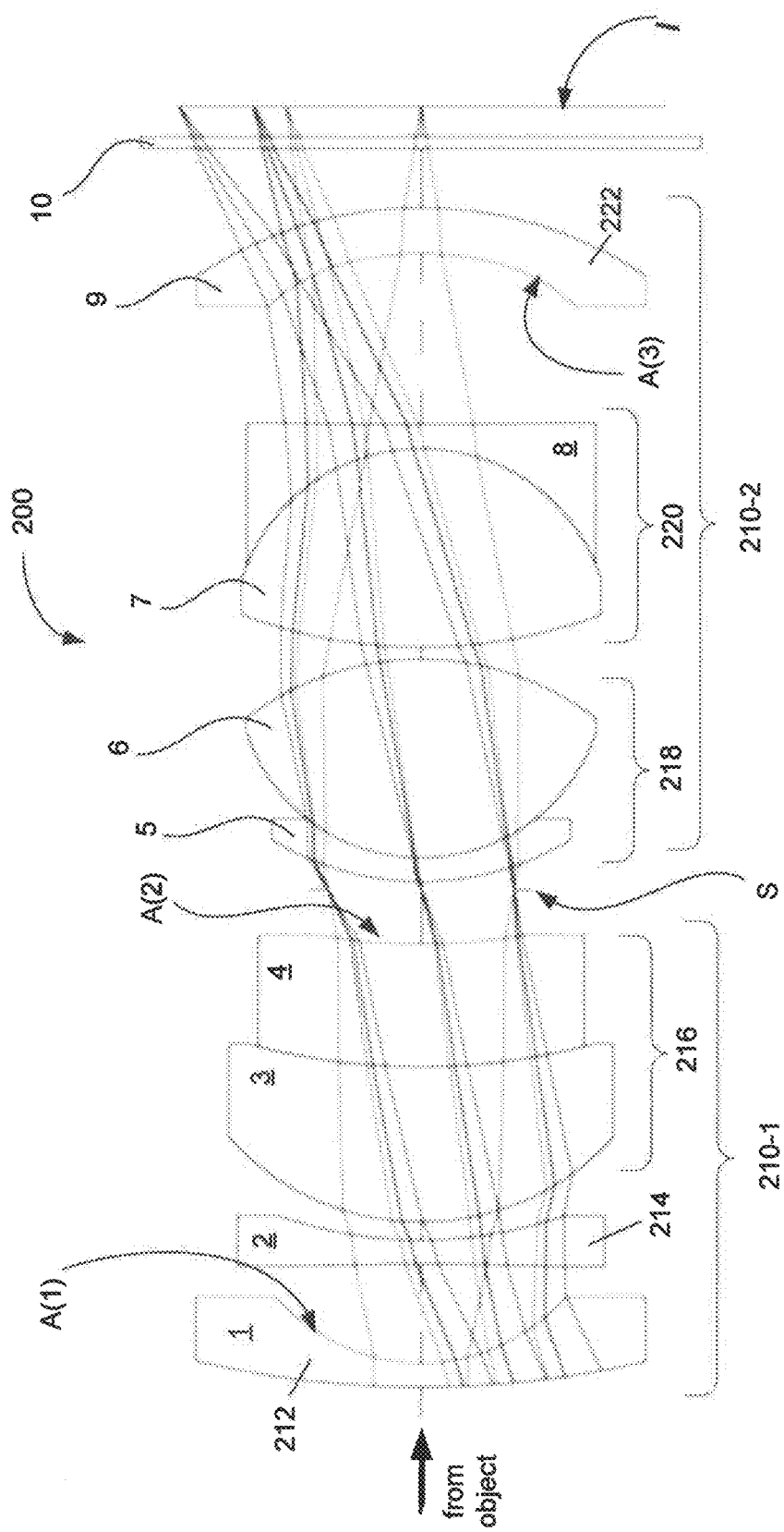
FIG. 2 is a diagram representing an embodiment of the non-telecentric optical objective of the endoscope probe of the system of FIG. 1.

The image formed with the use of a single objective such as that of FIG. 2 (or a stereo-image formed with the simultaneous use of two objectives 200) geometrically matches a 1080p high-definition visible sensor with 1.5 micron pixel pitch, and/or a half-720p near infrared sensor. There is no vignetting at the aperture stop, disposed between the first and second groups 210-1, 210-2 of the lens elements, and the objective is non-telecentric at the sensor plane (shown as an image plane I) to achieve the transverse dimensions of the lens system 200 (that is, diameters of the constituent lens elements) to be smaller than the transverse dimensions of the image field at plane I. The objective 200 has three aspheric (up to the 10th power, as shown in Table 1A) surfaces, shown as A(1), A(2), and A(3) in FIG. 2.

Figure 3:
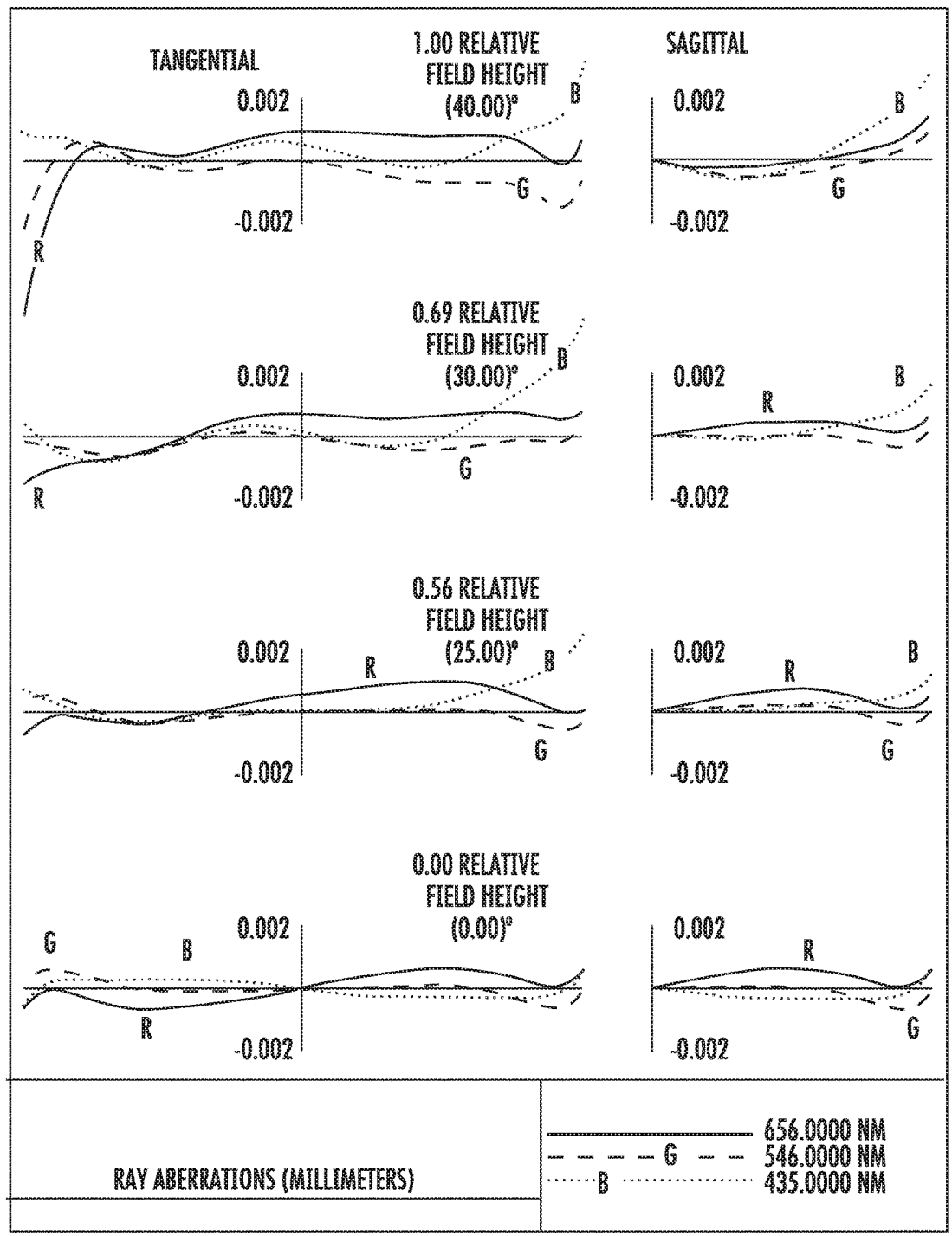
FIG. 3 contains plots illustrating ray aberrations characterizing the design of the embodiment of FIG. 2; plots labeled "R", "G", and "B" represent, respectively, ray aberrations at about 643.85 nm, 546.1 nm, and 479.99 nm wavelengths.
Figure 4:
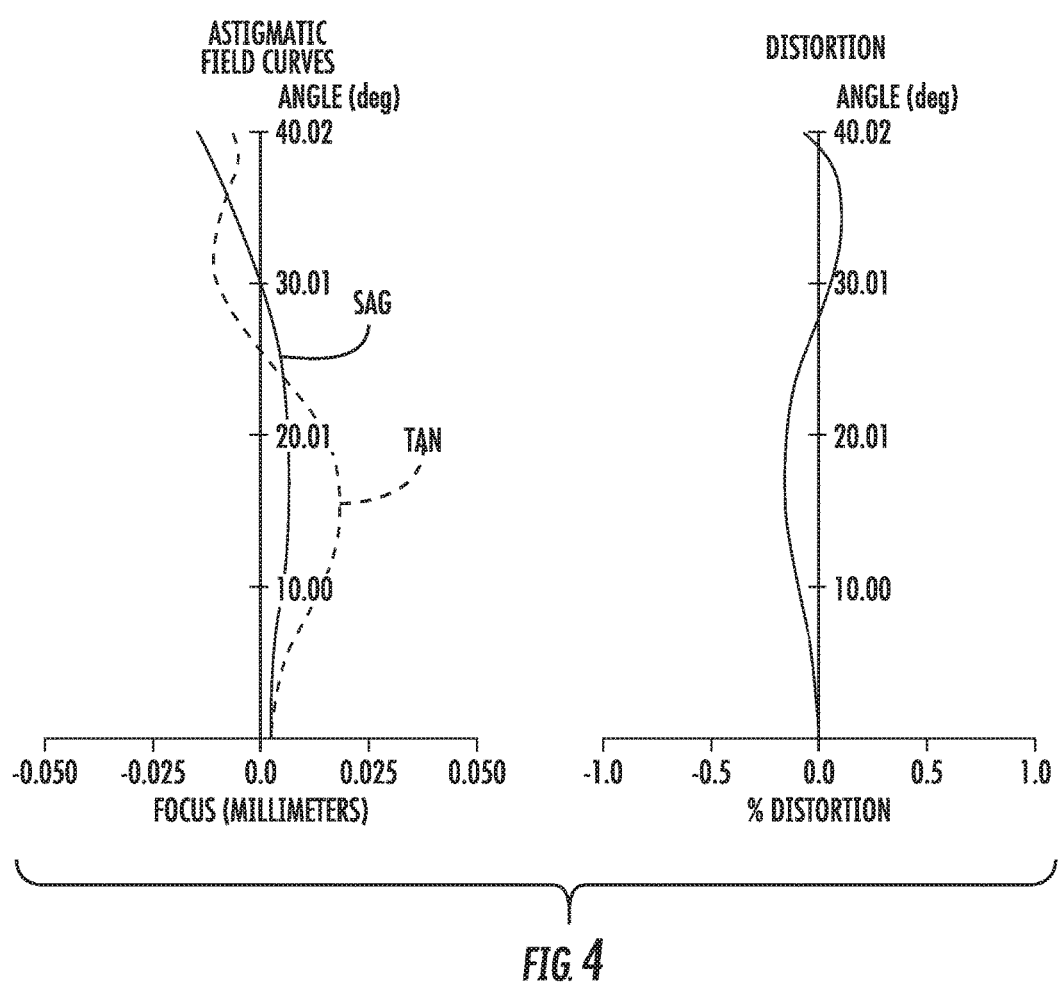
FIG. 4 presents field curves and a distortion curve characterizing the imaging properties of the embodiment of FIG. 2.

FIG. 3 illustrates ray aberrations representing optical performance of the embodiment 200. FIG. 4 illustrates the field curvature and distortion as a function of field angle. The distortion figure is notably within 0.25% for field angles up to 40 degrees (FIG. 4) which, in the case of distortion, is substantially below the level considered in related art to be a very good solution (while practically-acceptable level of distortion, targeted by the related art, is 5%). Lateral color aberration of the proposed design over the visible range (or at least within the range of wavelengths between about 435 nm and 656 nm) has a value comparable to the dimension of 1 pixel—or about 1.5 microns and, in practice, the possible increase of the lateral color aberration with increase in operational wavelength is corrected with the use of software processing optical images acquired by the sensor 126A.

Geometrical dimensions summarized in Table 1A evidence the practical compatibility of the objective design with dimensional requirements of the endoscope devices. The polychromatic analysis of performance of the embodiment over the visible portion of the spectrum, Table 1B, evidences that the operation of the objective is reliably characterized by a first Strehl ratio at the central wavelength (546.0 nm) and a second Strehl ratio across the chosen spectral bandwidth (in this example: 435.0 nm 656.0 nm), both of which are equal to or exceed 0.938 for the fields up to 40 degrees. At the same time, the polychromatic (second) Strehl ratio exceeds 0.96 for any field up to 30 degrees. At any value of the field angle up to 40 degrees the ratio of the Strehl ratio at a central wavelength to the Strehl ratio across the chosen visible bandwidth exceeds unity and, in this example, is within the range between about 1.001 and about 1.005. The monochromatic analysis of the performance of the embodiment over the visible portion of the spectrum, Table 1C, evidences that the operation of the objective is reliably characterized by the individual Strehl ratio (at the central wavelength chosen to be 546.0 nm) remaining at a value of at least 0.98 for any field up to 40 degrees, and at least 0.988 or higher for any field up to 30 degrees.

At the same time or alternatively, the wavefront analysis in the IR portion of the spectrum (Table 1D) shows that the operation of the embodiment 200 simultaneously exhibits the individual Strehl ratio (at the chosen IR wavelength) exceeding or equal to at least 0.967 for any field angle up to 40 degrees, while remaining equal to or above 0.994 for any field angle up to 25 degrees.

Figure 5:
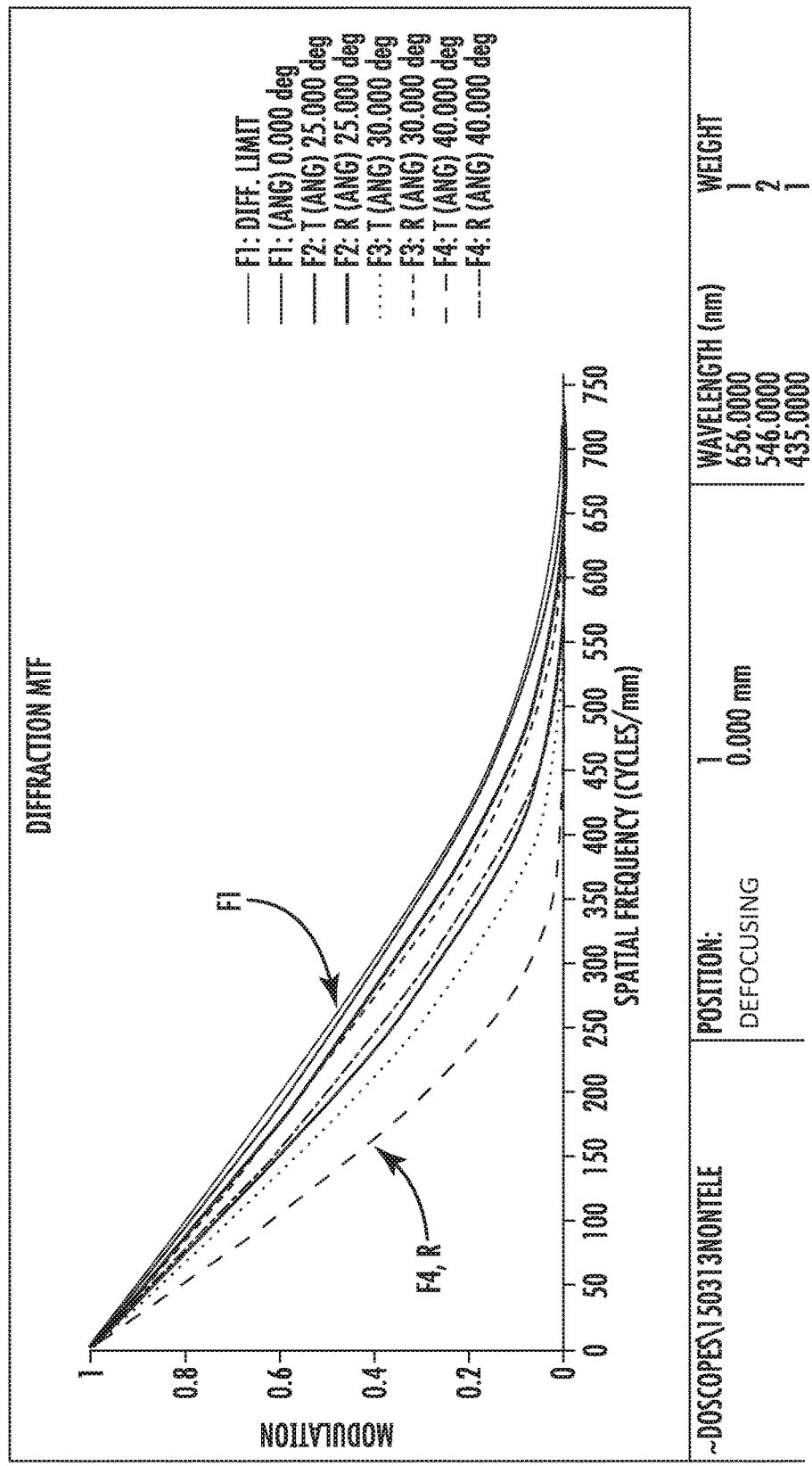
FIG. 5 shows plots representing a portion of the modulated transfer function (MTF) describing the operation of the embodiment of FIG. 2 in the visible portion of optical spectrum.
Figure 6:
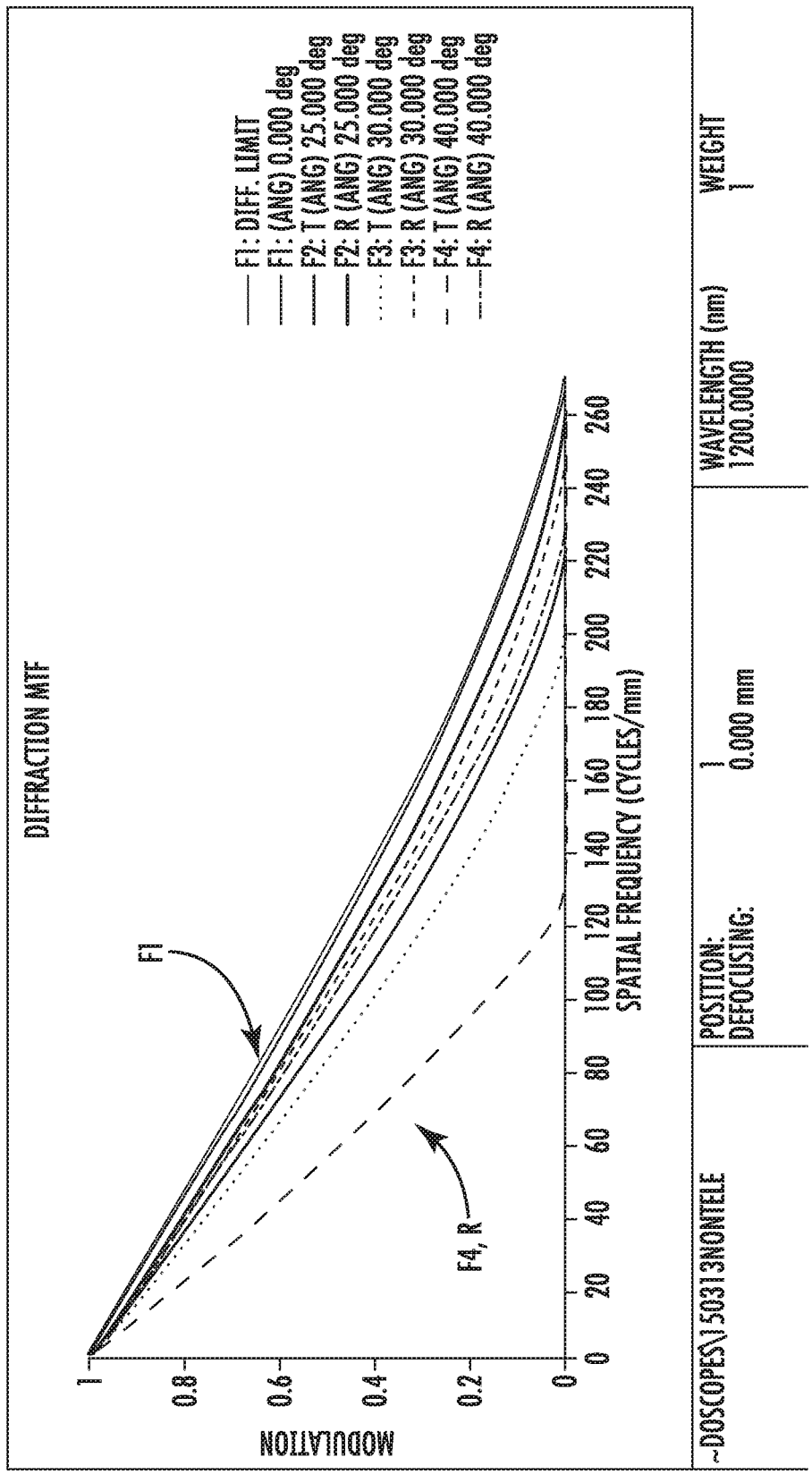
FIG. 6 shows plots representing a portion of the MTF describing the operation of the embodiment of FIG. 2 at 1200 nm.

For other aberrations, the identification of what is practically acceptable comes down to the modulated transfer function (MTF) curves. Based on the proposed design and in reference to FIGS. 5 and 6 (that illustrate respectively parameters of the MTF characterizing the operation of the embodiment 200 in the visible portion of the spectrum and in light at 1200 nm) the ideal solution is diffraction limited (the top curve in the MTF curves). Notably, the performance of the design on-axis is close to the ideal solution, with some falloff at the edge of the field—and would be considered practically acceptable by a person of ordinary skill in the art in visual and/or photographic optical systems. Specifically, the cut-off frequency of operation in the visible portion of the spectrum is always above about 500 cycles/mm (both for imaging in tangential and sagittal planes) and exceeding about 650 cycles/mm for imaging in the sagittal plane at any field angle up to 40 degrees, while simultaneously always being maintained above about 130 cycles/mm (both for imaging in tangential and sagittal planes and reaching about 200 cycles/mm for imaging in the sagittal plane) the chosen IR wavelength.

Such consideration, accepted in the art, at least in part is explained by the specifics of the practical use of the system, where user generally positions the optical system such that the object of interest is in the center of the field. Based on the satisfying performance demonstrated by the MTF curves of FIG. 6, the proposed design is operationally sound in both visible and near IR. Therefore, it is possible and contemplated that, depending on how the system is used, the system of FIG. 2 is made operably refocusable between a first state corresponding to operation at a visible wavelength and a second state corresponding to operation at an IR wavelength of choice.

Notably, in one embodiment the endoscope probe objective is non-telecentric at the sensor (in the image space), to accommodate an implementation in which the dimension of the lens is smaller than the dimension of the optical sensor acquiring the image formed by the lens. Therefore, it is understood that the embodiment is a compound lens that does not have its exit pupil at infinity (that is, at an infinite distance from such lens). Accordingly, the chief rays (oblique rays that pass through the center of the aperture stop) are not parallel to the optical axis of such lens behind the lens (in the image space), and the system is complemented with a micro-lens array (not shown) disposed between the lens and the image sensor.

In practice, the endoscope probe of the device of the invention may be configured by optically complementing the single objective 200 (in a mono-embodiment of the endoscope probe) or a pair of objectives 200 (in a stereo-embodiment of the probe) with corresponding optical fiber elements (such as multimode optical fiber(s), MMFs, or large-dimensions fiber-optic-bundle lightguides; not shown in FIG. 2) the entrance end facets of which have optical quality and disposed at the image plane I to collect light received from the object through the endoscope probe objective at the image plane and relay the formed image to the corresponding optical sensor. At least a portion of each optical fiber element is disposed within the endoscope probe housing or sheath—just like the objectives themselves—and further extend (optionally-within the same or another sheath) towards the optical detection unit 126.

It is appreciated, therefore, that the disclosed optical design that includes two groups of lens elements (each group having corresponding negative optical power) that are separated by the apertures stop provides an more symmetrical optical solution with low distortion on no more than 0.25% (which is much less than 1% of the related art) and with lens diameters smaller than the transverse dimensions of the optical sensor (to allow premium space for mechanical mounting of the lenses inside the endoscope probe and minimizing the cross-section of the probe). Image quality is further improved by the use of three mild aspheric surfaces. All glass types used in the design allow the use of a precision molding process to reduce manufacturing costs.

The application of such embodiments finds its use in the field of laparoscopic imaging with different markers/dyes, which have affinity to particular types of tissue, that requires both visible (VIS) and near-IR (NIR) optical channels. Different optical channels use different optical sensors (CCDs, InGaAs, etc. such as those discussed, for example, in U.S. patent application Ser. No. 15/099,346 the disclosure of which is incorporated herein by reference) and, while having equal focal lengths, are configured to image the target using different fixed focal positions.

Embodiments of this invention can be combined with embodiments of related art—for example, with embodiments of objectives described in Ser. No. 15/393,705 to produce an endoscope configured for stereoscopic imaging of a scene in optionally different FOVs and optionally different spectralbands. In one specific implementation, the endoscope probe includes, in addition to the embodiment of FIG. 2 having a first FOV, a second optical objective having a second FOV. These objectives are optically accommodated to form a respectively-corresponding image at respectively-corresponding first and second optical detectors associated with the endoscope probe. The specific embodiment can also include a programmable processor configured to receive, respectively, first and second optical data from the first and second optical detectors and to form a composite image in which a first portion of the image representing the first optical data is fused with a second portion of said image representing the second optical data.

It is appreciated that some of the steps of the embodiments of the method of the invention can be effectuated with a processor controlled by instructions stored in a tangible, non-transitory storage memory. The memory may be random access memory (RAM), read-only memory (ROM), flash memory or any other memory, or combination thereof, suitable for storing control software or other instructions and data. Some of the functions performed by the processor have been described with reference to flowcharts and/or block diagrams. Those skilled in the art should readily appreciate that functions, operations, decisions, etc. of all or a portion of each block, or a combination of blocks, of the flowcharts or block diagrams may be implemented as computer program instructions, software, hardware, firmware or combinations thereof. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

References made throughout this specification to "one embodiment," "an embodiment," "a related embodiment," or similar language mean that a particular feature, structure, or characteristic described in connection with the referred to "embodiment" is included in at least one embodiment of the present invention. Thus, appearances of these phrases and terms may, but do not necessarily, refer to the same implementation. It is to be understood that no portion of disclosure, taken on its own and in possible connection with a figure, is intended to provide a complete description of all features of the invention.

It is also to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed.

The invention as recited in claims appended to this disclosure is intended to be assessed in light of the disclosure as a whole, including features disclosed in prior art to which reference is made.

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

What is claimed:

1. An endoscope probe comprising:
   a sheath; and
   a first optical objective inside said sheath, the first optical objective including an aperture stop, and
   first and second groups of lens elements separated by said aperture stop,
   wherein
   the first group of lens elements has a first negative dioptric power and includes a first meniscus lens with a first positive dioptric power and a first optical doublet; and
   the second group of lens elements has a second positive dioptric power and includes immediately adjacent to one another second and third optical doublets,
   wherein the first optical objective is non-telecentric in image space, and
   wherein a diameter of any lens element of the first optical objective is smaller than a transverse dimension of an image formed at an image plane in light that has traversed the first optical objective.

2. An endoscope probe according to claim 1, devoid of a fourth optical doublet.

3. An endoscope probe according to claim 1, wherein the aperture stop separates the first optical doublet from the second optical doublet.

4. An endoscope probe according to claim 1, wherein the first optical doublet, the aperture stop, and the second optical doublet are disposed in a sequence and are immediately adjacent to one another in said sequence.

5. An endoscope probe according to claim 1, further comprising an optical fiber element disposed to collect light that has propagated through the first optical objective.

6. An endoscope probe according to claim 1, wherein each of the first and second groups of lens elements includes an aspheric refractive surface.

7. An endoscope probe according to claim 6, comprising only three aspheric refractive surfaces.

8. An endoscope probe according to claim 1,
   wherein the first optical objective exhibits distortion at or below 0.25% for field angles up to at least 40 degrees while, at the same time, having a ratio of the first and second Strehl ratios exceeding unity at any of said field angles, wherein the first Strehl ratio is defined at a central wavelength of a predetermined bandwidth of a visible spectrum, wherein the second Strehl ratio is defined across said predefined bandwidth of the visible spectrum.

9. An endoscope probe according to claim 1,
   wherein a polychromatic operation of said first objective is characterized by a first Strehl ratio and a second Strehl ratio both of which are equal to or exceed 0.938 for any field angle up to at least 40 degrees,
   wherein the first Strehl ratio is defined at a central wavelength of a predetermined bandwidth of a visible spectrum,
   wherein the second Strehl ratio is defined across said predefined bandwidth of the visible spectrum.

10. An endoscope probe according to claim 9, wherein the second Strehl ratio is above 0.96 at any field angle up to 30 degrees.

11. An endoscope probe system according to claim 1, wherein the first optical objective has a first field of view (FOV), and further comprising:
   a second optical objective having a second FOV, said first and second optical objectives optically accommodated to form respectively-corresponding images at respectively-corresponding first and second optical detectors associated with the endoscope probe; and
   a programmable processor configured to receive, respectively, first and second optical data from the first and second optical detectors and to form a composite image in which a first portion of said composite image representing the first optical data is fused with a second portion of said composite image representing the second optical data.

12. An endoscope probe according to claim 11, wherein a first combination of the first optical objective and the first optical detector and a second combination of the second optical objective with the second optical detector are configured to form, respectively, said first and second optical data carrying information in first and second spectral windows.

13. An endoscope probe according to claim 12, wherein the first and second spectral windows do not overlap.

14. An endoscope probe comprising:
a sheath; and
a first optical objective inside said sheath, the first optical objective including an aperture stop, and
first and second groups of lens elements separated by said aperture stop,
wherein
the first group of lens elements has negative dioptric power and includes a first meniscus lens with positive dioptric power and a first optical doublet; and
the second group of lens elements has positive dioptric power and includes immediately adjacent to one another second and third optical doublets
wherein the first optical objective exhibits distortion at or below 0.25% for field angles up to at least 40 degrees while, at the same time, having a ratio of the first and second Strehl ratios exceeding unity at any of said field angles,
wherein the first Strehl ratio is defined at a central wavelength of a predetermined bandwidth of a visible spectrum, and
wherein the second Strehl ratio is defined across said predefined bandwidth of the visible spectrum.

15. An endoscope probe according to claim 14, wherein at least one of the following conditions is satisfied:
a) wherein the first optical objective is non-telecentric in image space; and
b) wherein each of the first and second groups of lens elements includes an aspheric refractive surface.

16. An endoscope probe according to claim 14, wherein the first optical objective has a first field of view (FOV), and further comprising
a second optical objective having a second FOV, said optical objectives optically accommodated to form a respectively-corresponding image at respectively-corresponding first and second optical detectors associated with the endoscope probe; and
a programmable processor configured to receive, respectively, first and second optical data from the first and second optical detectors and to form a composite image in which a first portion of said image representing the first optical data is fused with a second portion of said image representing the second optical data.

17. An endoscope probe comprising:
a sheath; and a first optical objective inside said sheath, the first optical objective having a first field of view (FOV) and including an aperture stop, and first and second groups of lens elements separated by said aperture stop, wherein the first group of lens elements has a first negative dioptric power and includes a first meniscus lens with a first positive dioptric power and a first optical doublet;
and the second group of lens elements has a second positive dioptric power and includes immediately adjacent to one another second and third optical doublets, a second optical objective having a second FOV, said optical objectives optically accommodated to form respectively-corresponding images at respectively-corresponding first and second optical detectors associated with the endoscope probe; and a programmable processor configured to receive, respectively, first and second optical data from the first and second optical detectors and to form a composite image in which a first portion of said composite image representing the first optical data is fused with a second portion of said composite image representing the second optical data,
wherein a first combination of the first optical objective and the first optical detector and a second combination of the second optical objective with the second optical detector are configured to form, respectively, said first and second optical data carrying information in first and second spectral windows.

18. An endoscope probe according to claim 17, wherein at least one of the following conditions is satisfied: a) the endoscope probe is devoid of a fourth optical doublet; b) the aperture stop separates the first optical doublet from the second optical doublet; c) the first optical doublet, the aperture stop, and the second optical doublet are disposed in a sequence and are immediately adjacent to one another in said sequence; and d) the endoscope probe further comprises an optical fiber element disposed to collect light that has propagated through the first optical objective.

19. An endoscope probe according to claim 17, wherein at least one of the following conditions is satisfied:
a) wherein the first optical objective is non-telecentric in image space, and
b) wherein each of the first and second groups of lens elements includes an aspheric refractive surface.

* * * * *

UNITED STATES PATENT AND TRADEMARK OFFICE
CERTIFICATE OF CORRECTION

PATENT NO. : 10,386,626 B2
APPLICATION NO. : 15/425455
DATED : August 20, 2019
INVENTOR(S) : David M. Williamson Page 1 of 1

It is certified that error appears in the above-identified patent and that said Letters Patent is hereby corrected as shown below:

In the Claims

Column 16, Line 31 In Claim 11, first line:
"An endoscope probe system according to claim 1", should be -- An endoscope probe according to claim 1 --

Signed and Sealed this
Twenty-second Day of October, 2019

Andrei Iancu
*Director of the United States Patent and Trademark Office*